(12) United States Patent
Bristow (10) Patent No.: US 9,700,053 B2
(45) Date of Patent: *Jul. 11, 2017

(54) SYNERGISTIC HERBICIDAL COMPOSITION AND USE THEREOF

(71) Applicant: ROTAM AGROCHEM INTERNATIONAL COMPANY, LIMITED, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,204

(22) Filed: Oct. 29, 2015

(65) Prior Publication Data

US 2017/0118987 A1 May 4, 2017

(51) Int. Cl.
*A01N 41/10* (2006.01)
*A01N 47/36* (2006.01)

(52) U.S. Cl.
CPC ............ *A01N 47/36* (2013.01); *A01N 41/10* (2013.01)

(58) Field of Classification Search
CPC ........ A01N 41/10; A01N 47/36; A01N 25/04; A01N 25/08; A01N 25/12; A01N 25/14; A01N 25/22; A01N 25/30
See application file for complete search history.

(56) References Cited

U.S. PATENT DOCUMENTS

| | | |
|---|---|---|
| 4,762,838 A | 8/1988 | Glazer |
| 5,463,081 A | 10/1995 | Ort et al. |
| 2011/0086760 A1* | 4/2011 | Casana Giner ........ A01N 43/40 504/103 |
| 2011/0237436 A1* | 9/2011 | Olenik ................... A01N 25/12 504/231 |
| 2014/0005050 A1* | 1/2014 | Sohm ..................... A01N 41/10 504/133 |

FOREIGN PATENT DOCUMENTS

WO WO 2006021743 A1 * 3/2006 ........... C07C 315/06

OTHER PUBLICATIONS

Roberts, R.M. et al. Modern Experimental Organic Chemistry. Holt, Rinehart and Winston, New York, 1979, pp. 49-58.*
S.R. Colby: Calculating Synergistic and Antagonistic Response of Herbicide Combinations, Weeds 1967,15, 20-22.
Vippagunta et al.: Crystalline Solids, Advance Drug Delivery Reviews (2001), vol. 48, pp. 3-26.
Herbicide Handbook, Weed Science Society of America, Seventh Edition 1994, p. 318.

* cited by examiner

*Primary Examiner* — John Pak
*Assistant Examiner* — Nathan W Schlientz
(74) *Attorney, Agent, or Firm* — Dickinson Wright PLLC (57) ABSTRACT

A herbicidal composition is provided, the composition comprising: (A) the crystalline modification I of 2-(4-mesyl-2-nitrobenzoyl)cyclohexane-1,3-dione (mesotrione); and (B) the crystalline modification I of sodium salt of methyl 4-iodo-2-[[[[(4-methoxy-6-methyl-1,3,5-triazin-2-yl)amino] carbonyl]amino]sulfonyl]benzoate (iodosulfuron-methyl-sodium). A method of controlling plant growth at a locus comprises applying to the locus herbicidally effective amounts of both (A) the crystalline modification I of 2-(4-mesyl-2-nitrobenzoyl)cyclohexane-1,3-dione (mesotrione); and (B) the crystalline modification I of sodium salt of methyl 4-iodo-2-[[[[(4-methoxy-6-methyl-1,3,5-triazin-2-yl)amino] carbonyl]amino]sulfonyl]benzoate (iodosulfuron-methyl-sodium).

32 Claims, 3 Drawing Sheets

SYNERGISTIC HERBICIDAL COMPOSITION AND USE THEREOF

BACKGROUND

1. Field

The present disclosure relates to a synergistic herbicidal composition containing mesotrione and Iodosulfuron-methyl-sodium, each in particular crystal modifications. The composition finds use in controlling the growth of undesirable plant, particularly in crops, including using the aforementioned composition.

2. Description of Related Art

The protection of crops from undesirable plant, which inhibits crop growth, is a constantly recurring problem in agriculture. To solve this problem, researchers are trying to produce an extensive variety of chemicals and chemical formulations effective in the control of such undesirable growth. Chemical herbicides of many types have been disclosed in the literature and a large number are in commercial use.

Some herbicidal active ingredients have been shown to be more effective when applied in combination rather than applied individually, this effect being referred to as "synergism." According to *Herbicide Handbook* of the Weed Science Society of America, Seventh Edition, 1994, page 318, "synergism" is an interaction of two or more factors such that the effect when combined is greater than the predicted effect based on the response to each factor applied separately.

The compound 2-(4-mesyl-2-nitrobenzoyl)cyclohexane-1,3-dione has the common name "mesotrione". Mesotrione is a substance that can form polymorph crystals. Two different forms, crystalline modifications I and II, of mesotrione are described in WO2006021743, which is incorporated herein by reference for all purposes. Mesotrione is active as a herbicide and is now commercially available in a range of formulations for controlling the growth of undesirable plant.

The compound sodium salt of methyl 4-iodo-2-[[[[(4-methoxy-6-methyl-1,3,5-triazin-2-yl)amino]carbonyl]amino]sulfonyl]benzoate, having the common name "iodosulfuron-methyl-sodium", is a member of the sulfonylurea group of chemicals. Iodosulfuron-methyl-sodium is a potent herbicide having high selectivity, high efficiency, low toxicity and other desirable attributes. It is used post-emergence on crops, such as vegetables and cereals, against a variety of annual and perennial grasses and broadleaved weeds. It is rather less toxic towards algae and is of generally low toxicity towards most other wildlife. The commercially available iodosulfuron-methyl-sodium, which is usually manufactured by the process described in U.S. Pat. No. 5,463,081, which is incorporated herein by reference, where it is present in an amorphous state.

It has been found that iodosulfuron-methyl-sodium in the amorphous state is highly unstable. It will generally undergo significant hydrolysis when dissolved or dispersed in water. Furthermore, hydrolysis can occur during storage, particularly where the compound is exposed to moisture. It has been found that a crystalline form of iodosulfuron-methyl-sodium, termed hereinafter "crystalline modification I", has an improved stability in formulations (U.S. Ser. No. 14/926,133, filed on even date herewith, and incorporated herein by reference in its entirety for all purposes). The crystalline modification I of iodosulfuron-methyl-sodium of the invention exhibits at least 3 of the following reflexes as $2\theta$ values in an X-ray powder diffractogram recorded using Cu-K$\alpha$ radiation at 25° C.:

$$2\theta = 11.558 \pm 0.2 \tag{1}$$

$$2\theta = 14.569 \pm 0.2 \tag{2}$$

$$2\theta = 18.045 \pm 0.2 \tag{3}$$

$$2\theta = 19.442 \pm 0.2 \tag{4}$$

$$2\theta = 20.633 \pm 0.2 \tag{5}$$

$$2\theta = 23.226 \pm 0.2 \tag{6}$$

$$2\theta = 26.145 \pm 0.2 \tag{7}$$

$$2\theta = 27.199 \pm 0.2 \tag{8}$$

$$2\theta = 27.877 \pm 0.2 \tag{9}$$

$$2\theta = 29.090 \pm 0.2 \tag{10}$$

SUMMARY

It has been surprisingly found that combining the crystalline modification I of mesotrione with the crystalline modification I of iodosulfuron-methyl-sodium provides a composition having a synergistic activity, that is, an increased herbicidal activity, compared with the activity expected from the activity of the two components when applied individually.

Accordingly, in a first aspect, the present invention provides a herbicidal composition comprising:

(A) the crystalline modification I of 2-(4-mesyl-2-nitrobenzoyl)cyclohexane-1,3-dione (mesotrione); and (B) the crystalline modification I of sodium salt of methyl 4-iodo-2-[[[[(4-methoxy-6-methyl-1,3,5-triazin-2-yl)amino]carbonyl]amino]sulfonyl]benzoate (iodosulfuron-methyl-sodium).

The composition of an embodiment of the invention is of particular use for controlling the growth of undesirable plant.

In a second aspect, the invention provides a method of controlling the growth of undesirable plant comprising applying to the plant or to the locus thereof a herbicidally effective amount of the herbicidal composition of the first aspect of the present invention.

In a further aspect, the invention provides the use of the herbicidal composition of the first aspect of the invention in control of undesirable plant growth at a locus.

DETAILED DESCRIPTION OF SPECIFIC EMBODIMENTS

The references to the crystalline modifications I and II of mesotrione as used herein, refer to the crystalline modification of mesotrione disclosed in WO2006021743, which is incorporated herein by reference in its entirety for all purposes, where they are described as Form I and Form II, respectively. The XRD diffraction data for mesotrione crystal form I from this publication are given below, although some peak shifting may be possible.

| Peak Position (2-Theta) | Peak Position (d spacing) |
|---|---|
| 8.52 | 10.34 |
| 17.08 | 5.18 |
| 17.43 | 5.08 |
| 18.74 | 4.73 |
| 19.04 | 4.66 |
| 19.31 | 4.59 |
| 19.52 | 4.54 |
| 21.15 | 4.20 |
| 25.73 | 3.46 |
| 28.66 | 3.11 |

Alternatively, the crystalline modification I mesotrione may have a slightly shifted XRD spectrum:

| Peak Position (2-Theta) | Peak Position (d spacing) |
|---|---|
| 8.44 | 10.47 |
| 17.35 | 5.11 |
| 17.55 | 5.05 |
| 18.67 | 4.75 |
| 18.98 | 4.68 |
| 19.24 | 4.61 |
| 19.45 | 4.56 |
| 21.06 | 4.22 |
| 25.64 | 3.47 |
| 28.55 | 3.13 |

The term "herbicide" as used herein, refers to a compound that controls the growth of plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

The term "plants" refers to all physical parts of a plant, including shoots, leaves, needles, stalks, stems, fruit bodies, fruits, seeds, roots, tubers and rhizomes.

The term "locus" refers to the place on which the plants are growing, the place on which the plant propagation materials of the plants are sown or the place on which the plant propagation materials of the plants will be sown.

"At least one" designates a number of the respective compounds or components of 1, 2, 3, 4, 5, 6, 7, 8, 9 or more, preferably 1, 2, or 3.

The synergistic herbicidal composition, the method and use of the present invention are suitable for controlling undesirable plant growth in a range of crops, including: cereals, for example wheat, barley, rye, oats, corn, rice, sorghum, triticale and related crops; fruit, such as pome fruit, stone fruit and soft fruit, such as apples, pears, plums, peaches, pistachio, almonds, cherries, and berries, for example grape, banana, strawberries, bushberry, caneberry, raspberries and blackberries; leguminous plants, for example beans, lentils, peas, and soybeans; oil plants, for example oilseed rape, mustard and sunflowers; cucurbitaceae, for example cantaloupe, marrows, cucumbers, melons, pumpkin, squash and watermelon; citrus fruit, such as oranges, lemons, grapefruit and mandarins; and vegetables, for example spinach, lettuce, asparagus, cabbages, carrots, onions, tomatoes, potatoes, paprika, garlic and leeks; coffee; sugarcane; hops; tree nuts; as well as ornamentals, for example flowers, such as roses, shrubs, broad-leaved trees and evergreens, such as conifers. Preferably, the composition described herein is used to treat cereals, sugarcane and vegetables. More preferably, the composition described herein is used to treat wheat, barley, rye, oats, corn, triticale, sorghum, sugarcane, and asparagus.

The control of undesirable plant growth in such crops may be achieved by applying to the locus (A) the crystalline modification I of 2-(4-mesyl-2-nitrobenzoyl)cyclohexane-1,3-dione (mesotrione), which is identified as Form I in WO 2006/021743 and (B) the crystalline modification I of sodium salt of methyl 4-iodo-2-[[[[(4-methoxy-6-methyl-1,3,5-triazin-2-yl)amino] carbonyl]amino]sulfonyl]benzoate (iodosulfuron-methyl-sodium) in suitable amounts.

The active compounds (A) and (B) may be applied to the locus together or separately. If applied separately, active compounds (A) and (B) may be applied at the same time and/or consecutively. The control may comprise applying to the undesirable plant or the locus thereof a herbicidally effective amount of the herbicidal composition.

It has been surprisingly found that a combination of (A) the crystalline modification I of 2-(4-mesyl-2-nitrobenzoyl)cyclohexane-1,3-dione (mesotrione) and (B) the crystalline modification I of sodium salt of methyl 4-iodo-2-[[[[(4-methoxy-6-methyl-1,3,5-triazin-2-yl)amino] carbonyl] amino]sulfonyl]benzoate (iodosulfuron-methyl-sodium) exhibits a synergistic action in the control of many weeds, particularly, but not limit to, broadleaved weeds and grasses. For example, weeds treatable according to an embodiment of the invention include:

African Rue (*Peganum Harmala*), Alkali Mallow (*Malvella leprosa*), Alligatorweed (*Alternantha philoxeroides*), Alsike Clover (*Trifolium hybridum*), Amaranth (*Amaranthus* spp), Annual Broomweed (*Gutierrezia dracunculoides*), annual knawel, annual mercury (*Mercurialis annua*), Annual Pricklepoppy (*Argemone polyanthemos*), Annual Sowthistle (*Sonchus oleraceus*), Antelope Horn (*Asclepias viridis*), Asiatic Hawksbeard (*Youngia japonica*), Balsam Gourd (*Ibervillea lindheimeri*), Balsam-Apple (*Momordica charantia*), Bastard Toadflax (*Comandra umbellata*), Beggarweed (*Desmodium* spp.), Bindweed, Field (noxious) (*Convolvulus arvensis*), Bindweed, Hedge (*Convolvulus sepium*), Bindweed, Texas (*Convolvulus equitans*), Birdsfoot Trefoil (*Lotus corniculatus*), Bittercress, Small-flowered (*Cardamine parviflora*), Bitterweed (*Hymenoxys odorata*), Bitterweed, Brown (*Helenium badium*), Black Medic (*Medicago lupulina*), black mustard, Black Nightshade (*Solanum americanum*), Blackfoot Daisy (*Melampodium leucanthum*), Blackseed Plantain (*Plantago rugelii*), Bladderpod (*Lesquerella gracilis*), blue/purple mustard, Bracted Plantain (*Plantago aristata*), broadleaf dock, Broadleaf Plantains (*Plantago* spp.), Buckhorn Plantain (*Plantago lanceolata*), Buffalo Gourd (*Cucurbita foetidissima*), Buffalobur (*Solanum rostratum*), Bulbous Buttercup (*Ranunculus bulbosus*), Bull Thistle (*Cirsium vulgare*), bur buttercup, Bur Clover (*Medicago hispida*), Burcucumber (*Sicyos angulatus*), Bushy Buttonweed (*Spermacoce assurgens*), Bushy Wallflower (*Erysimum repandum*), bushy wallflower, Butterweed (*Senecio glabellus*), Camphorweed (*Heterotheca subaxillaris*), Canada Thistle (*Cirsium arvense*), Carolina False Dandelion (*Pyrrhopappus carolinianus*), Carolina *geranium*, Carpetweed (*Mollugo verticillata*), Catchweed Bedstraw (*Galium aparine*), Centella, Chamberbitter (*Phyllanthus urinaria*), Chicory (*Cichorium intybus*), Cinquefoil, Clammy Groundcherry (*Physalis heterophylla*), clasping pepperwee, Climbing Hempweed (*Mikania scandens*), coast fiddleneck, Coat Buttons (*Tridax procumbens*), Common Beggar-tick (*Bidens alba*), common buckwheat, Common Burdock (*Arctium minus*), Common Chickweed (*Stellaria media*), Common Cocklebur (*Xanthium strumarium*), Common Groundsel (*Senecio vulgaris*), Common Lambsquarters (*Chenopodium album*), Common Mallow, Common Milkweed (*Asclepias syriaca*), Common Mullein (*Verbascum thapsus*), common orache (*Atriplex patula*), Common Pokeweed (*Phytolacca americana*), Common Purslane (*Portulaca oleracea*), common radish, Common Ragweed (*Ambrosia artemiisifolia*), Common Sneezeweed (*Helenium amarum*), Common Sunflower (*Helianthus annuus*), Common Waterhemp (*Amaranthus rudis*), Common Yarrow (*Achillea millefolium*), Compass Plant (*Silphium laciniatum*), conical catchfly, Coreopsis (*Coreopsis tinctoria*), corn chamomile, Corn Gromwell (*Lithospermum arvense*), Corn Speedwell (*Veronica arvensis*), corn spurry, Cowcockle (*Vaccaria pyramidata*), Cowpen Daisy (*Verbesina encelioides*), Creeping Beggarweed (*Desmodium incanum*), creeping buttercup (*Ranunculus repens*), Creeping Cucumber (*Melothria pendula*), Creeping Indigo (*Indigofera spicata*), Creeping Oxalis, Creeping Speedwell, Creeping Woodsorrel (*Oxalis corniculata*), cress, Croton, Texas (*Croton texensis*), Croton, Tropic (*Croton glandulosus*), Croton, Woolly (*Croton capitatus*), Cup Plant (*Silphium perfoliatum*), Cupid's Shaving Brush (*Emilia sonchifolia*), Curly Dock (*Rumex crispus*), Curlycup Gumweed (*Grindelia squarrosa*), Cutleaf Eveningprimose (*Oenothera laciniata*), Cutleaf Groundcherry (*Physalis angulata*), Daisy Fleabane (*Erigeron annuus*), Dakota Verbena (*Verbena bipinnatifida*), Dandelion (*Taraxacum officinale*), Dayflower (*Commelina*), Deadnettle, Purple (*Lamium purpureum*), Devil's Claw (*Proboscidea louisianica*), Dichondra, Dogfennel (*Euphorbia capillifolium*), Elderberry (*Sambucus canadensis*), Englemann Daisy (*Englemannia pinnatifida*), false chamomile, False Daisy or *Eclipta* (*Eclipta prostrata*), False Nightshade (*Chamaesaracha coronopus*), field chickweed, Field Dodder (*Cuscuta campestris*), field pennycress, Filaree, California or Redstem (*Erodium cicutarium*), Filaree, Texas or Storkbill (*Erodium texanum*), fixweed, Flixweed (*Descurainia sophia*), Florida Pellitory (*Parietaria floridana*), Garden Rocket (*Eruca vesicaria* ssp. *sativa*), Garden Spurge (*Chamaesyce hirta*), Germander (*Teucrium cubense*), Giant Ragweed (*Ambrosia trifida*), Goldenrod (*Solidago* spp.), goosefoots (*Chenopodium* spp.), Gray Tidestrom (*Tidestromia lanuginosa*), Greenbriar (*Smilax* spp.), Greenthread (*Thelesperma filifolium*), Ground Spurge (*Euphorbia prostrata*), groundsel, Hairy Caltrop (*Kallstroemia hirsutissina*), Hairy Nightshade (*Solanum sarrachoides*), Hedge Parsley (*Torilis arvensis*), Hemp Dogbane (*Apocynum cannabinum*), Hemp Sesbania (*Sesbania exaltata*), Henbit (*Lamium amplexicaule*), Hogpotato (*Hoffmanseggia densiflora*), Honeysuckle (*Lonicera* spp.), Hophornbeam Copperleaf (*Acalypha ostryaefolia*), Horehound (*Marrubium vulgare*), Horse purslane (*Trianthema portulacastrum*), Horsenettle (*Solanum carolinense*), Horseweed (*Conyza canadensis*), Huisachedaisy (*Amblyolepis setigera*), Hyssop Spurge (*Chamaesyce hyssopifolia*), Illinois Bundleflower (*Desmanthus illinoensis*), Indian Blanket (*Gaillardia pulchella*), Indian Mallow (*Abutilon incana*), Japanese Hops (*Humulus japonicus*), Jerusalem Artichoke (*Helianthus tuberosus*), Jimsonweed (*Datura stramonium*), Khakiweed (*Alternanthera pungens*), knotweed (*polygonum* spp.), Kochia (*Kochia scoparia*), Kudzu (noxious) (*Pueraria lobata*), Lamb's-quarters (*Chenopodium album*), Lanceleaf Sage (*Salvania reflexa*), Lantana (*Lantana camara*), Livid Amaranth (*Amaranthus blitum*), Lizardtail Gaura (*Gaura Parviflora*), London rocket, Long Fruited Primrose-Willow (*Ludwigia octovalvis*), Marijuana (noxious) (*Cannabis sativa*), Marsh Parsley (*Cyclospermum leptophylum*), marshelder, Match-Head (*Phyla nodiflora*), mayweed chamomile, Mexicanhat (*Ratibida columnaris*), Mexican-Poppy (*Argemone mexicana*), miners lettuce, Mock Bishop's Weed (*Ptilimnium capillaceum*), Morningglory, Bigroot (*Ipomoea pandurata*), Morningglory, Ivyleaf (*Ipomoea hederacea*), Morningglory, Morningglory, entireleaf (*Ipomoea hederacea* var. *integriuscul*), Pitted (*Ipomoea lacunosa*), Morningglory, Sharppod (*Ipomoea trichocarpa*), Morningglory, Tall (*Ipomoea purpurea*), Mouseear Chickweed (*Cerastium vulgatum*), Mousetail (*Myosurus minimus*), Multiflora rose (noxious) (*Rosa multiflora*), Mustard, London Rocket (*Sisymbrium irio*), Mustard, Pinnatetansy (*Descurainia pinnate*), Mustard, Tansy (*Descurainia pinnata*), Mustard, Tumble (*Sisymbrium altissimum*), Mustard, Turnip Weed (*Rapistrum rugosum*), Mustard, Wild (*Brassica kaber*), narrowleaf lambsquarters, ightflowering catchfly, Nodding Spurge (*Euphorbia nutans*), Orange Globe Mallow (*Sphaeralcea occidentalis*), Oxeye Daisy (*Chrysanthemum leucanthemum*), Palmer Amaranth (*Amaranthus palmeri*), Partridgepea (*Cassia chamaecrista*), Pennsylvania smartweed, Pennycress, Field (*Thlaspi arvense*), pigweed, Pigweed, Prostrate (*Amaranthus blitoides*), Pigweed, Redroot (*Amaranthus retroflexus*), Pigweed, Tumble (*Amaranthus albus*), pineappleweed, plains *coreopsis*, Poison Hemlock (*Conium maculatum*), prickly lettuce, Prickly Pear (*Opuntia* spp.), Prickly Sida (*Sida spinosa*), Prostrate Knotweed (*Polygonum aviculare*), Puncturevine (*Tribulus terrestris*), Purple Flower Groundcherry (*Physalis lobata*), Purple Horsemint (*Monarda citriodora*), Purple Loosestrife (noxious) (*Lythrum salicaria*), Purslane Speedwell (*Veronica peregrina*), Rain Lily (*Cooperia drummondii*), Rattlesnake master (*Eryngium yuccifolium*), Red Hornedpoppy (*Glaucium corniculatum*), redmaids, Riddell Groundsel (*Senecio riddellii*), Rosinweed (*Silphium integrifolium*), rough cocklebur (*Xanthium strumarium*), Russian thistle, Saltmarsh Fleabane (*Pluchea odorata*), Santa Maria or *Parthenium* Pancake Weed (*Parthenium hysterophorus*), Sawtooth aster (*Prionopsis ciliata*), Scarlet Gaura (*Gaura coccinea*), Scarlet Musk Flower (*Nyctaginia capitata*), scentless chamomile, Scrambledeggs (*Corydalis curvisiliqua*), Shepherd's Purse (*Capsella bursa-pastoris*), Sicklepod (*Senna obtusifolia*), SilverLeaf Cassia (*Cassia phyllodinea*), Silverleaf Nightshade (*Solanum elaeagnifolium*), Silversage (*Artemesia ludoviciana*), Silversheath Knotweed (*Polygonum argyrocoleon*), Skeletonweed (*Lygodesmia juncea*), Slender Aster (*Aster gracilis*), smallflower buttercup, Smallhead Sneezeweed (*Helenium microcephalum*), Smallseed Falseflax (*Camelina microcarpa*), smartweed, Smartweed, Pale (*Polygonum lapathifolium*), Smartweed, Pennsylvania (*Polygonum pensylvanicum*), Smooth Groundcherry (*Physalis subglabrata*), Smooth Sumac (*Rhus glabra*), snow speedweed, Snow-on-the-mountain (*Euphorbia marginata*), Southern Sida (*Sida acuta*), Spiny Pigweed (*Amaranthus spinosus*), Spiny Sowthistle (*Sonchus asper*), Sprawling Horseweed (*Calyptocarpus vialis*), Spreading Dayflower (*Commelina diffusa*), Spurge, Leafy (*Euphorbia esula*), Spurge, Prostrate (*Euphorbia humistrata*), Spurge, Toothed (*Euphorbia dentata*), Spurred Anoda (*Anoda cristata*), sticky chickweed, stinking mayweed/dogfennel, Sweet-potato (*Ipomea batatas*), swinecress, Tahoka Daisy (*Machaeranthera tanacetifolia*), tansymustard, tarweed fiddleneck, Texas Blueweed (*Helianthus ciliaris*), Texas Bullnettle (*Cnidoscolus texanus*), Thistle, Blessed Milk (*Silybum marianum*), Thistle, Distaff (*Carthamus lanatus*), Thistle, Malta Star (*Centaurea melitensis*), Thistle, Musk (noxious) (*Carduus nutans*), Thistle, Scotch (noxious) (*Onopordum acanthium*), Thistle, Tall (*Cirsium altissimum*), Thistle, Texas Purple (*Cirsium texanum*), Threadleaf Groundsel (*Senecio longilobus*), Toothcup (*Ammannia latifolia*), Trumpetcreeper (*Campsis radicans*), tumble, Twinleaf Sennia (*Senna roemeriana*), Velvetleaf (*Abutilon theophrasti*), Venice Mallow (*Hibiscus trionum*), Vetch (*Vicia* spp.), Virginia Copperleaf (*Acalypha virginica*), Virginia Creeper (*Parthenocissus quinquefolia*), Virginia Pepperweed (*Lepidium virginicum*), volunteer adzuki bean (*Vigna angularis*), volunteer lentils, volunteer peas, volunteer sunflower, Wandering Cudweed (*Gnaphalium pensylvanicum*), Waterhemlock (*Cicuta maculata*), Waterhemp (*Amaranthus tuberculatus*), Waterleaf (*Nama hispidum*), waterpod, Western Ragweed (*Ambrosia psilostachya*), Western Salsify (*Tragopogon dubuis*), White Foxglove Beardtongue (*Penstemon digitalis*), White Heath Aster (*Aster pilosus*), White Snakeroot (*Eupatorium rugosum*), Wild Buckwheat (*Polygonum convolvulus*), Wild Carrot (*Daucus carota*), wild chamomile, wild garlic, Wild Geranium (*Geranium carolinanum*), Wild Lettuce (*Lactuca serriola*), wild mustard (*Sinapis arvensis*), wild radish, Woollyleaf Bursage (*Ambrosia grayi*), Woollywhite, Chalkhill (*Hymenopappus tenuifolius*), Woollywhite, Yellow (*Hymenopappus flavescens*), Wright Eryngo (*Eryngium heterophyllum*), Yellow Rocket (*Barbarea vulgaris*), Yellow Sweetclover (*Melilotus indica*), Amaranth, powell (*Amaranthus powellii*), Atriplex (*Chenopodium orach*), Broadleaf signalgrass (*Urochloa platyphylla*), Buffalobur (*Solanum rostratium*), Crabgrass, large (*Digitaria sanguinalis*), Galinsoga (*Galinsoga parviflora*), Morningglory, entireleaf (*Ipomoea hederacea* var. *integriuscula*), Nightshade, black (*Solanum nigrum*), Nightshade, Eastern black (*Solanum ptycanthum*), Nutsedge, yellow (*Cyperus esculentus*), Pigweed, smooth (*Amaranthus hybridus*), Perennial rye-grasses (*Lolium perenne*), Italian rye-grasses (*Lolium multiflorum*), Loose silky-bent (*Agrostis spica-venti*), Canary grass (*Phalaris paradoxa*), Black-bindweed (*Fallopia convolvulus*), Common field-speedwell (*Veronica persica*), Cut-leaved cranesbill (*Geranium dissectum*), Field pansy (*Viola arvensis*), Fool's parsley (*Aethusa cynapium*), Fumitory (*Fumaria officinalis*), Hemp-nettle, Common (*Galeopsis tetrahit*), Ivy-leaved speedwell (*Veronica hederifolia*), Redshank (*Persicaria maculosa*), Runch (*Raphanus raphanistrum*), Scentless mayweed (*Tripleurospermum inodorum*), Stinking mayweed (*Anthemis cotula*), Volunteer oilseed rape (*Brassica napus*), Cleavers (*Galium aparine*).

Preferably, such weeds include *Chenopodium* spp., *Polygonum* spp., *Stellaria* spp., *Amaranthus* spp., *Amaranthus* spp., *Ipomoea* spp., *Veronica* spp., *Fallopia* spp., *Brassica* spp., *Galium* spp., *Xanthium* spp.

More preferably, such weeds include Atriplex (*Chenopodium album*), Knotweed, prostrate (*Polygonum aviculare*), Chickweed, common (*Stellaria media*), Amaranth, powell (*Amaranthus powellii*), Pigweed, red root (*Amaranthus retroflexus*), Morningglory, Ivyleaf (*Ipomoea hederacea*), Ivy-leaved speedwell (*Veronica hederifolia*), Black-bindweed (*Fallopia convolvulus*), Mustard, wild (*Brassica kaber*), Cleavers (*Galium aparine*), Cocklebur, common (*Xanthium strumarium*), Volunteer oilseed rape (*Brassica napus*).

The total amount of (A) and (B) is from 5% to 99% by weight of the composition.

The crystalline modification I of mesotrione may be present in the synergistic herbicidal composition of the present invention in any suitable amount, and is generally present in an amount of from about 1% to about 90% by weight of the composition, preferably from about 1% to 80% by weight, more preferably from about 1% to about 70% by weight of the composition.

The crystalline modification I of iodosulfuron-methyl-sodium may be present in the synergistic herbicidal composition in any suitable amount, and is generally present in an amount of from about 0.1% to about 90% by weight of the composition, preferably from about 1% to about 80% by weight, more preferably from about 1% to about 70% by weight of the composition, more preferably from about 1% to about 60%.

(A) and (B) may be employed in the composition, method or use of the present invention in any suitable weight ratio. The weight ratio of the crystalline modification I of mesotrione and the crystalline modification I of iodosulfuron-methyl-sodium in the composition may be in the range of from about 150:1 to about 1:50, preferably from about 100:1 to about 1:25, more preferably from about 50:1 to about 1:10, more preferably still from about 15:1 to about 1:3, preferably from about 10:1 to about 1:1, about 7.5:1 to about 1:1, most preferably 10:1.

In general, the application rate of the active ingredients depends on such factors as the type of weed, type of crop plant, soil type, season, climate, soil ecology and various other factors. The application rate of the composition for a given set of conditions can readily be determined by routine trials.

In general the composition or the method of the present invention can be applied at an application rate of from about 0.005 kilograms/hectare (kg/ha) to about 5.0 kg/ha of the total amount of active ingredient (A) and (B) being applied. Preferably, the application rate is from about 0.01 kg/ha to 3.0 kg/ha of the active ingredients.

Preferably, the application rate of the active ingredients is from 1 to 1000 g/ha of (A) the crystalline modification I of mesotrione and from 0.1 to 250 g/ha of (B) the crystalline modification I of iodosulfuron-methyl-sodium. More preferably, the application rate of the active ingredients is from 1 to 250 g/ha of (A) the crystalline modification I of mesotrione and from 1 to 100 g/ha of (B) the crystalline modification I of iodosulfuron-methyl-sodium. Even more preferably, the application rate of the active ingredients is from 1 to 150 g/ha of (A) the crystalline modification I of mesotrione and from 1 to 80 g/ha of (B) the crystalline modification I of iodosulfuron-methyl-sodium.

As noted above, in an embodiment of the invention, (A) the crystalline modification I of mesotrione and (B) the crystalline modification I of iodosulfuron-methyl-sodium may be applied either separately or combined as part of a two-part herbicidal system, such as the composition of the present invention. The composition is applied pre-planting, pre-emergence and/or post-emergence.

The compositions of an embodiment of this invention can be formulated in conventional manner, for example by mixing (A) the crystalline modification I of mesotrione and (B) the crystalline modification I of iodosulfuron-methyl-sodium with appropriate auxiliaries. Suitable auxiliaries will depend upon such factors as the type of formulation and will be known to the person skilled in the art.

In particular, the composition may further comprise one or more auxiliaries selected from extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents. Such auxiliaries are known in the art and are commercially available. Their use in the formulation of the compositions of the present invention will be apparent to the person skilled in the art.

Suitable formulations for applying a combination of (A) and (B) include water-soluble concentrates (SL), emulsifiable concentrates (EC), emulsions (EW), micro-emulsions (ME), suspension concentrates (SC), oil-based suspension concentrates (OD), flowable suspensions (FS), water-dispersible granules (WG), water-soluble granules (SG), wettable powders (WP), water soluble powders (SP), granules (GR), encapsulated granules (CG), fine granules (FG), macrogranules (GG), aqueous suspo-emulsions (SE), capsule suspensions (CS) and microgranules (MG). Preferred formulations are suspension concentrates (SC), water-dispersible granules (WG) and water-soluble granules (SG).

The composition may comprise one or more inert fillers. Such inert fillers are known in the art and available commercially. Suitable fillers include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks, and mixtures thereof.

The composition may optionally include one or more surfactants which are preferably non-ionic, cationic and/or anionic in nature and surfactant mixtures which have good emulsifying, dispersing and wetting properties, depending upon the active compound/compounds being formulated. Suitable surfactants are known in the art and are commercially available.

Suitable anionic surfactants can be both so-called water-soluble soaps and water-soluble synthetic surface-active compounds. Soaps which may be used include the alkali metal, alkaline earth metal or substituted or unsubstituted ammonium salts of higher fatty acid ($C_{10}$ to $C_{22}$), for example the sodium or potassium salt of oleic or stearic acid, or of natural fatty acid mixtures.

The surfactant may comprise an emulsifier, dispersant or wetting agent of ionic or nonionic type. Examples of such agents include salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, and phosphoric esters of polyethoxylated phenols or alcohols.

The presence of at least one surfactant is generally required when the active compound and/or the inert carrier and/or auxiliary/adjuvant are insoluble in water and the vehicle for the final application of the composition is water.

The composition may optionally further comprise one or more polymeric stabilizers. Suitable polymeric stabilizers that may be used in the present invention include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foaming agents for use in the compositions include all substances which can normally be used for this purpose in agrochemical compositions. Suitable anti-foaming agents are known in the art and are available commercially. Particularly preferred antifoam agents are mixtures of polydimethylsiloxanes and perfluroalkylphosphonic acids, such as the silicone anti-foaming agents available from GE or Compton.

Suitable solvents for use in the compositions may be selected from all customary organic solvents which thoroughly dissolve the active compounds employed. Again, suitable organic solvents for (A) and (B) are known in the art. The following may be mentioned as being preferred: N-methyl pyrrolidone, N-octyl pyrrolidone, cyclohexyl-1-pyrrolidone; and a mixture of paraffinic, isoparaffinic, cycloparaffinic and aromatic hydrocarbons (available commercially as SOLVESSO™200). Suitable solvents are commercially available.

Suitable preservatives include all substances which can normally be used for this purpose in agrochemical compositions of this type and again are well known in the art. Suitable examples that may be mentioned include PREVENTOL® (from Bayer AG) and PROXEL® (from Bayer AG).

The compositions may comprise an antioxidant. Suitable antioxidants are all substances which can normally be used for this purpose in agrochemical compositions, as is known in the art. Preference is given to butylated hydroxytoluene.

Suitable thickening agents for use in the compositions include all substances which can normally be used for this purpose in agrochemical compositions. Examples include xanthan gum, PVOH, cellulose and its derivatives, clay hydrated silicates, magnesium aluminum silicates or a mixture thereof. Again, such thickening agents are known in the art and available commercially.

The compositions may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica, or cement.

In addition, depending upon the formulation, the composition according to the invention may also comprise water.

The formulated composition may for example be applied in spray form, for example employing appropriate dilutions using a diluent, such as water.

In the method and use of an embodiment of the invention, the combination of the active ingredients can be applied to the locus where control is desired, such as to the leaves of plants and/or the surrounding soil, by a convenient method.

In the event, (A) and (B) are applied simultaneously in an embodiment of the invention, they may be applied as a composition containing (A) and (B), in which case (A) and (B) can be obtained from a separate formulation source and mixed together (known as a tank-mix, ready-to-apply, spray broth, or slurry), optionally with other pesticides, or (A) and (B) can be obtained as a single formulation mixture source (known as a pre-mix, concentrate, formulated compound (or product)), and optionally mixed together with other pesticides.

In a preferred embodiment, the method and use of the present invention employ a composition according to the present invention.

The compositions according to an embodiment of the invention are distinguished by the fact that they are especially well tolerated by plants being treated and are environmentally friendly.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined by the appended claims.

Embodiments of the present invention will now be described, for illustrative purposes only, by way of the following examples.

EXAMPLES

Example 1—Preparation of the Crystalline Modification I Mesotrione

The crystalline modification I of mesotrione was prepared according to the method as mentioned in WO2006021743.

Mesotrione enolate suspension was filtered to remove any excess solid enolate. 50 mL of the filtered solution was placed in a reaction flask and heated to 40° C. The pH of the solution was adjusted to 2.8 by adding 10% HCl over 20 minutes. The crystals were allowed to stir for 20 minutes before isolation by filtration. The crystals were then washed with water and sucked dry on the filter.

Example 2—Preparation of the Crystalline Modification II Mesotrione

The crystalline modification II of mesotrione was prepared according to the method as mentioned in WO2006021743.

Mesotrione crystals were stirred with water in a reaction flask. The pH was increased to 12 by adding NaOH. 1.5 mL of 10% HCl was added over 15 minutes to reduce the pH of the solution to pH 4. Crystals were obtained.

Example 3—Preparation of iodosulfuron-methyl-sodium

Iodosulfuron-methyl-sodium in an amorphous form was prepared according to a method mentioned in U.S. Pat. No. 5,463,081.

Methyl 2-amino-4-iodobenzoate (Example 3 in U.S. Pat. No. 5,463,081)

A solution of 16.1 g of 2-acetylamino-4-iodobenzoic acid (melting point 233° C.-235° C.; synthesized in accordance with U.S. Pat. No. 4,762,838) in 325 ml of absolute methanol was saturated at 0° C. with dry hydrogen chloride gas. The mixture was heated to the boil for 15 hours, cooled to room temperature, resaturated using dry hydrogen chloride gas, and allowed to stand at room temperature for 24 hours. The solvent was evaporated in vacuo, the residue was taken up in dichloromethane, and the organic phase was washed with a saturated aqueous sodium hydrogen carbonate solution until free from acid. The organic phase was dried over $Na_2SO_4$, and evaporated in vacuo. This gave 13.8 g of methyl 2-amino-4-iodobenzoate of melting point 63° C.-67° C.

Bis(2-methoxycarbonyl-5-iodobenzene)disulfide (Example 4 in U.S. Pat. No. 5,463,081)

13.8 g of methyl 2-amino-4-iodobenzoate were treated with 48 ml of glacial acetic acid and subsequently with 86 ml of concentrated hydrochloric acid. A solution of 3.8 g of sodium nitrite in 15 ml of water was slowly added dropwise to this suspension which was cooled to −5° C., and stirring was continued at this temperature for 30 minutes. This cooled diazonium salt solution was added dropwise at 0° C. to a solution of 20 ml of sulfur dioxide, 60 ml of glacial acetic acid, 10 ml of water and 3.1 g of copper(II) chloride dihydrate, and stirring was continued first for 1 hour at 0° C. and then overnight at room temperature. The reaction mixture was poured into 1 l of ice-water, and the product was filtered off with suction. This gave 12.7 g of bis(2-methoxycarbonyl-5-iodobenzene)disulfide of melting point 133° C.-135° C.

2-Methoxycarbonyl-5-iodobenzenesulfochloride (Example 5 in U.S. Pat. No. 5,463,081)

Chlorine gas was passed at 20° C.-25° C. into 12.2 g of bis(2-methoxycarbonyl-5-iodobenzene)disulfide in a solution of 30 ml of 1,2-dichloroethane and 15 ml of 2N hydrochloric acid until the exothermic reaction has ended. The solids were filtered off with suction, the aqueous phase was extracted using dichloromethane, the combined organic phases were dried over $Na_2SO_4$, and the solvent was evaporated in vacuo. This gave a total amount of 15.0 g of 2-methoxycarbonyl-5-iodobenzenesulfochloride, from the filtered and extracted product, of melting point 119° C.-120° C.

2-Methoxycarbonyl-5-iodobenzenesulfonamide (Example 6 in U.S. Pat. No. 5,463,081)

Ammonia gas was passed at room temperature into 15.0 g of 2-methoxycarbonyl-5-iodobenzenesulfochloride in 100 ml of tetrahydrofuran until ammonia was no longer taken up. The solution was evaporated in vacuo, the residue was stirred thoroughly with water, and the product was filtered off with suction. After drying of the filter residue at 70° C. in vacuo, 10.7 g of 2-methoxycarbonyl-5-iodobenzenesulfonamide were obtained as a white powder of melting point 176° C.-177° C.

Iodosulfuron-methyl (Example 9 of U.S. Pat. No. 5,463,081)

A solution of 1.7 g of 1,8-diazabicyclo[5.4.0]undec-7-ene in 10 ml of absolute acetonitrile was added dropwise at room temperature to a mixture of 3.4 g of 5-iodo-2-methoxycarbonyl benzenesulfonamide and 2.8 g of O-phenyl (4-methyl-6-methoxy-1,3,5-triazin-2-yl)-carbamate in 50 ml of absolute acetonitrile. The mixture was stirred at this temperature for 3 hours, concentrated to approx. ⅓ and poured into 200 ml of ice-water. The aqueous phase was extracted using diethyl ether, the pH was brought to 1-2 using concentrated hydrochloric acid, and the product was filtered off with suction. After drying in vacuo at 60° C., 3.3 g of iodosulfuron-methyl were obtained.

Iodosulfuron-methyl-sodium (in Accordance with the Disclosure of Suzhou Daxue Xuebao, Ziran Kexueban (2009), 25(1), 66-68, 94)

23 g of iodosulfuron-methyl (0.04 mol, 93%) was dissolved in 200 mL acetone completely. 4.0 g (0.05 mol) 50%

NaOH solution was added dropwise. keep the reaction for 30 mins. The reaction flask was cooled down to below 0° C. at ice-water bath. The precipitate was filtered and collected. 21.0 g of iodosulfuron-methyl-sodium was obtained after drying.

Figure 3:
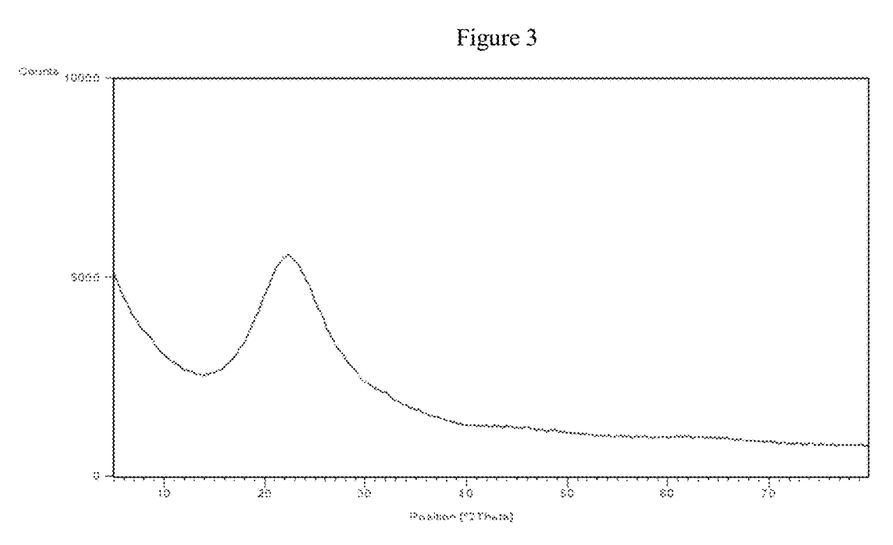
FIG. 3 is an X-ray powder diffractogram of amorphous iodosulfuron-methyl-sodium.

As shown in FIG. 3, the X-ray powder diffraction pattern of the resulting iodosulfuron-methyl-sodium product has no significant signals, which indicates the iodosulfuron-methyl-sodium product prepared in accordance with the disclosure of U.S. Pat. No. 5,463,081 is amorphous.

Example 4—Preparation of the Crystalline Modification I of iodosulfuron-methyl-sodium 10 ml methanol was charged into the reactor to dissolve crude, amorphous iodosulfuron-methyl-sodium prepared in Example 3 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with methanol. The resulting solid was dried under high vacuum to give crystals of pure iodosulfuron-methyl-sodium technical (Purity: 98%).

The crystals were characterized as being of the crystalline modification I of iodosulfuron-methyl-sodium using both IR spectrometry and X-ray powder diffraction.

Figure 1:
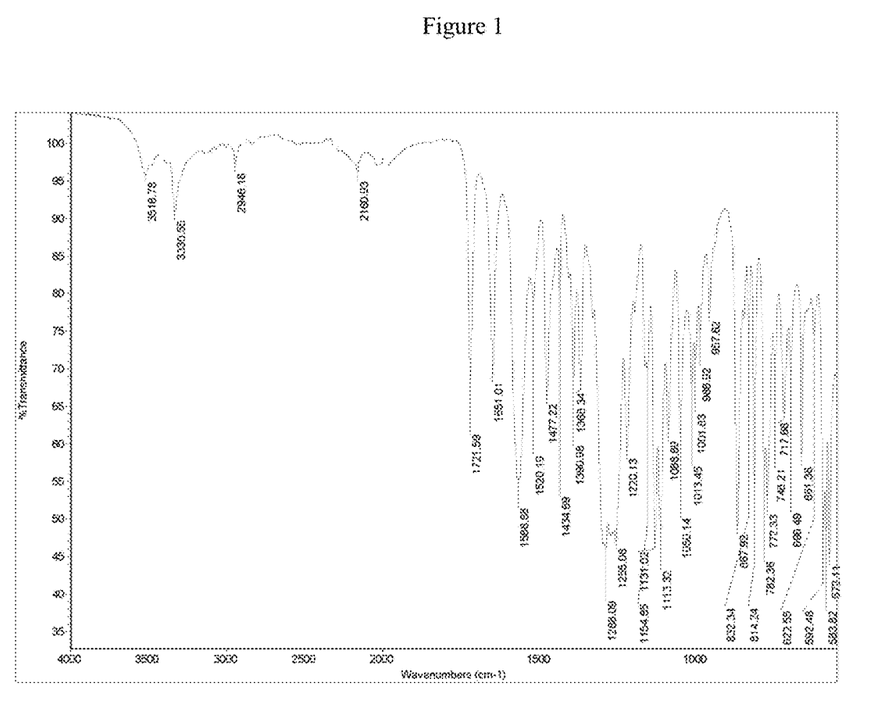
FIG. 1 is an infrared (IR) spectrograph of crystalline modification I of iodosulfuron-methyl-sodium, according to an embodiment of the invention.

The IR spectrum of the crystalline modification I of iodosulfuron-methyl-sodium is set out in FIG. 1. The IR spectrum exhibits characteristic peaks at 3516.78, 3330.55, 2946.18 and 2160.93 $cm^{-1}$.

Figure 2:
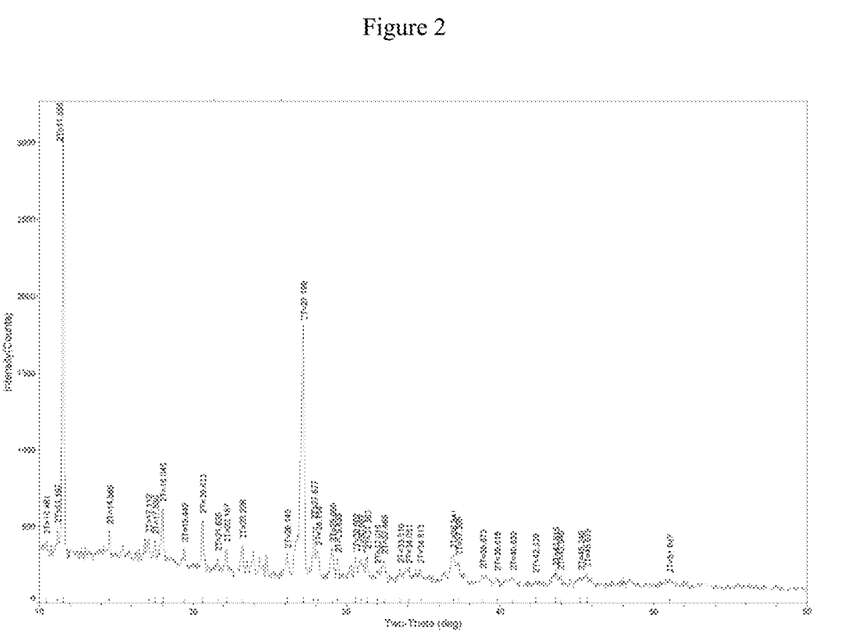
FIG. 2 is an X-ray powder diffractogram (XRD) of crystalline modification I of iodosulfuron-methyl-sodium, according to an embodiment of the invention.

The crystalline modification I of iodosulfuron-methyl-sodium has the X-ray powder diffractogram shown in FIG. 2 with the reflexes listed in Table 1 below.

TABLE 1

Powder X-ray diffractogram reflexes of crystalline modification I of iodosulfuron-methyl-sodium Crystalline modification I

| $2\theta$ (°) | d (Å) |
|---|---|
| 11.588 ± 0.2 | 8.88 ± 0.05 |
| 14.569 ± 0.2 | 7.05 ± 0.05 |
| 18.045 ± 0.2 | 5.70 ± 0.05 |
| 19.442 ± 0.2 | 5.30 ± 0.05 |
| 20.633 ± 0.2 | 4.99 ± 0.05 |
| 23.226 ± 0.2 | 4.44 ± 0.05 |
| 26.145 ± 0.2 | 3.96 ± 0.05 |
| 27.199 ± 0.2 | 3.80 ± 0.05 |
| 27.877 ± 0.2 | 3.71 ± 0.05 |
| 29.090 ± 0.2 | 3.56 ± 0.05 |

Formulation Examples

Water-dispersible granule (WG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), Potassium carbonate (balance to 100%)) under compressed air, then wetting, extruding and drying to obtain water-dispersible granule.

For example,

| | |
|---|---|
| The crystalline modification I of mesotrione | 50% |
| The crystalline modification I of iodosulfuron-methyl-sodium | 1% |
| SUPRALATE ® (sodium lauryl sulfate, Witco Inc., Greenwich) | 0.5% |
| REAX ®88B (sodium lignosulfonate, Westvaco Corp) | 5% |
| Potassium carbonate | Balance to 100% |

Aqueous suspension concentrates (SC) were prepared by mixing finely ground active ingredients with auxiliaries (10% Propylene glycol, 5% Tristyrylphenol ethoxylates, 1% Sodium lignosulfonate, 1% Carboxymethylcellulose, 1% Silicone oil (in the form of a 75% emulsion in water), 0.1% Xanthan gum, 0.1% NIPACIDE BIT 20, Water (Balance to 1 L).

For example,

| | |
|---|---|
| The crystalline modification I of mesotrione | 40% |
| The crystalline modification I of iodosulfuron-methyl-sodium | 4% |
| Propylene glycol | 10% |
| Tristyrylphenol ethoxylates | 5% |
| Sodium lignosulfonate | 1% |
| Carboxymethylcellulose | 1% |
| Silicone oil (in the form of a 75% emulsion in water) | 1% |
| Xanthan gum | 0.1% |
| NIPACIDE BIT 20 | 0.1% |
| Water | Balance to 1 L |

Water-soluble granules (SG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), 2% Sodium hydrogen carbonate ($NaHCO_3$), Potassium sulfate (balance to 100%)) under compressed air, then wetting, extruding and drying to obtain water-soluble granules.

For example,

| | |
|---|---|
| The crystalline modification I of mesotrione | 30% |
| The crystalline modification I of iodosulfuron-methyl-sodium | 4% |
| SUPRALATE ® (sodium lauryl sulfate, Witco Inc., Greenwich) | 0.5% |
| REAX ® 88B (sodium lignosulfonate, Westvaco Corp) | 5% |
| Sodium hydrogen carbonate ($NaHCO_3$) | 2% |
| Potassium sulfate | Balance to 100% |

Formulations were prepared according to the method above (Table A):

TABLE A

| No. | Formulation type | Mesotrione (%) I | Mesotrione (%) II | Iodosulfuron-methyl-sodium (%) Amorphous | Iodosulfuron-methyl-sodium (%) I |
|---|---|---|---|---|---|
| 1 | SC | 40 | / | / | / |
| 2 | SC | / | 40 | / | / |
| 3 | WG | / | / | 60 | / |
| 4 | WG | / | / | / | 60 |
| 5 | SC | 40 | / | 4 | / |
| 6 | SC | / | 40 | 4 | / |
| 7 | SC | 40 | / | / | 4 |
| 8 | SC | / | 40 | / | 4 |
| 9 | SC | 40 | / | / | 4 |
| 10 | WG | 50 | / | / | 1 |
| 11 | SC | 40 | / | / | 0.4 |
| 12 | SG | 30 | / | / | 4 |
| 13 | WG | 60 | / | / | 6 |
| 14 | SC | 20 | / | / | 20 |
| 15 | SG | 10 | / | / | 30 |

Biological Examples 1

A synergistic effect exists with a combination of two active compounds when the activity of a composition comprising both active compounds is greater than the sum of the activities of the two active compounds applied individually. The expected activity for a given combination of two active compounds can be calculated by the so called "Colby equation" (see S. R. Colby, "Calculating Synergistic and Antagonistic Responses of Herbicide Combinations", Weeds 1967, 15, 20-22):

whereby:

A=the efficiency % of compound A when active compound A is employed at an application rate of m g/ha;

B=the efficiency % of compound B when active compound B is employed at an application rate of n g/ha;

E=the efficiency % of estimated activity when compounds A and B are employed together at an application rate of m g/ha and n g/ha;

then:

$$E = A + B - (A \times B / 100).$$

If the actual activity observed for the combination of compunds A and B is greater than that calculated, then the activity of the combination is superadditive. In other words, synergism is present.

Barley, wheat, corn and sorghum plants were sown side by side in the field. Different types of weeds were recorded and are listed in Table 1 below. Formulations of Examples 1 to 8 above were applied 50 days after planting. After application, the beds were maintained for about 2 weeks. Two weeks after application, the beds were examined to determine the efficiency of the treatment. The results are set forth below in Table 2 below.

TABLE 1

| Type of weed |
| --- |
| *Chenopodium album* |
| *Amaranthus retroflexus* |
| *Polygonum aviculare* |
| *Amaranthus powellii* |
| *Stellaria media* |
| *Brassica napus* |

TABLE 2

| | | | Efficiency (%) | | | | | |
| --- | --- | --- | --- | --- | --- | --- | --- | --- |
| | | Iodosulfuron- | | | Efficiency (%) Type of weed | | | |
| Formulation Examples | Mesotrione (g/ha) | methyl-sodium (g/ha) | *Chenopodium album* | *Amaranthus retroflexus* | *Polygonum aviculare* | *Amaranthus powellii* | *Stellaria media* | *Brassica napus* |
| Untreated | 0 | 0 | 0 | 0 | 0 | 0 | 0 | 0 |
| Example 1 | 100 | 0 | 30 | 35 | 30 | 25 | 30 | 35 |
| Example 2 | 100 | 0 | 35 | 35 | 30 | 25 | 25 | 25 |
| Example 3 | 0 | 10 | 25 | 25 | 25 | 20 | 20 | 25 |
| Example 4 | 0 | 10 | 30 | 30 | 25 | 25 | 25 | 30 |
| Example 5 | 100 | 10 | 65 | 70 | 65 | 60 | 65 | 65 |
| Example 6 | 100 | 10 | 55 | 55 | 55 | 50 | 55 | 55 |
| Example 7 | 100 | 10 | 95 | 100 | 100 | 95 | 100 | 95 |
| Example 8 | 100 | 10 | 60 | 70 | 70 | 65 | 70 | 70 |

Asparagus, oat, sugarcane and rye plants were sown side by side in the field. Different types of weeds were recorded and are listed in Table 3 below. Formulations of Examples 9 to 15 above were applied 50 days after planting. After application, the beds were maintained for about 2 weeks. Two weeks after application, the beds were examined to determine the efficiency of the treatment. The results are set forth below in Table 4 below.

TABLE 3

| Type of weed |
| --- |
| *Ipomoea hederacea* |
| *Veronica hederifolia* |
| *Fallopia convolvulus* |
| *Brassica kaber* |
| *Galium aparine* |
| *Xanthium strumarium* |

TABLE 4

| | | | Efficiency (%) | | | | | |
| --- | --- | --- | --- | --- | --- | --- | --- | --- |
| | | Iodosulfuron- | | | Efficiency (%) Type of weed | | | |
| Formulation Examples | Mesotrione (g/ha) | methyl-sodium (g/ha) | *Ipomoea hederacea* | *Veronica hederifolia* | *Fallopia convolvulus* | *Brassica kaber* | *Galium aparine* | *Xanthium strumarium* |
| Untreated | 0 | 0 | 0 | 0 | 0 | 0 | 0 | 0 |
| Example 9 | 100 | 10 | 100 | 95 | 95 | 95 | 100 | 100 |

TABLE 4-continued

| | | | Efficiency (%) | | | | | |
|---|---|---|---|---|---|---|---|---|
| | | Iodosulfuron- | Efficiency (%) Type of weed | | | | | |
| Formulation Examples | Mesotrione (g/ha) | methyl-sodium (g/ha) | *Ipomoea hederacea* | *Veronica hederifolia* | *Fallopia convolvulus* | *Brassica kaber* | *Galium aparine* | *Xanthium strumarium* |
| Example 10 | 125 | 2.5 | 80 | 90 | 90 | 85 | 90 | 80 |
| Example 11 | 150 | 1.5 | 85 | 80 | 85 | 85 | 85 | 85 |
| Example 12 | 75 | 10 | 95 | 90 | 95 | 90 | 95 | 90 |
| Example 13 | 150 | 15 | 95 | 100 | 100 | 95 | 100 | 95 |
| Example 14 | 30 | 30 | 90 | 85 | 90 | 85 | 90 | 85 |
| Example 15 | 20 | 60 | 75 | 70 | 80 | 75 | 80 | 70 |

The invention claimed is:

1. A composition comprising a herbicidally effective amount of
   (A) the crystalline modification I of 2-(4-mesyl-2-nitrobenzoyl)cyclohexane-1,3-dione (mesotrione); and
   (B) the crystalline modification I of sodium salt of methyl 4-iodo-2-[[[[(4-methoxy-6-methyl-1,3,5-triazin-2-yl)amino]carbonyl]amino]sulfonyl]benzoate (iodosulfuron-methyl-sodium), wherein the crystalline modification I of iodosulfuron-methyl-sodium exhibits each of the following reflexes as 2θ values in an X-ray powder diffractogram:

11.588±0.2

14.569±0.2

18.045±0.2

19.442±0.2

20.633±0.2

23.226±0.2

26.145±0.2

27.199±0.2

27.877±0.2

29.090±0.2.

2. The composition according to claim 1, wherein the weight ratio of (A) to (B) is in the range of from about 150:1 to about 1:50.

3. The composition according to claim 2, wherein the weight ratio of (A) to (B) is in the range of from 50:1 to about 1:10.

4. The composition according to claim 3, wherein the weight ratio of (A) to (B) is 10:1.

5. The composition according to claim 1, wherein the total amount of (A) and (B) is from 5% to 99% by weight of the composition.

6. The composition according to claim 5, wherein the composition comprises, by weight, from about 1% to about 90% of (A) and from about 0.1% to about 90% of (B).

7. The composition according to claim 5, wherein the composition comprises, by weight, from about 1% to about 70% of (A) and from about 1% to about 60% of (B).

8. The composition according claim 1, further comprising one or more auxiliaries selected from the group consisting of extenders, carriers, solvents, surfactants, stabilizers, antifoaming agents, anti-freezing agents, preservatives, antioxidants, colorants, thickening agents, solid adherents, fillers, wetting agents, dispersing agents, lubricants, anticaking agents and diluents.

9. The composition according to claim 1, formulated as a water-soluble concentrate (SL), an emulstifiable concentrate (EC), an emulsion (EW), a micro-emulsion (ME), a suspension concentrate (SC), an oil-based suspension concentrate (OD), a flowable suspension (FS), a water-dispersible granule (WG), a water-soluble granule (SG), a wettable powder (WP), a water soluble powder (SP), a granule (GR), an encapsulated granule (CG), a fine granule (FG), a macrogranule (GG), an aqueous suspo-emulsion (SE), a capsule suspension (CS) or a microgranule (MG).

10. A method of controlling undesirable plant growth comprising applying to the plant or to the locus thereof a herbicidally effective amount of the herbicidal composition of claim 1.

11. The method according to claim 10, wherein the plant growth is being controlled in a crop selected from the group consisting of cereals, sugarcane and vegetables.

12. The method according to claim 10, wherein the plant growth being controlled is selected from the group consisting of one or more of broadleaf weeds and grasses.

13. The method according to claim 12, wherein the plant growth being controlled is selected from the group consisting of one or more of *Chenopodium* spp., *Polygonum* spp., *Stellaria* spp., *Amaranthus* spp., *Amaranthus* spp., *Ipomoea* spp., *Veronica* spp., *Fallopia* spp., *Brassica* spp., *Galium* spp., *Xanthium* spp.

14. The method according to claim 10, wherein the composition is applied at an application rate of 0.005 kilograms/hectare (kg/ha) to about 5.0 kg/ha of the total amount of active ingredient (A) and (B).

15. The method according to claim 14, wherein the composition is applied at an application rate of from 0.01 kg/ha to 3.0 kg/ha of the total amount of active ingredient (A) and (B).

16. The method according to claim 15, wherein the composition is applied at an application rate of from 1 to 1000 g/ha of (A) and from 0.1 to 250 g/ha of (B).

17. The method according to claim 16, wherein the composition is applied at an application rate of from 1 to 150 g/ha of (A) and 1 to 80 g/ha of (B).

18. The method according to claim 10, wherein the composition is applied pre-planting, pre-emergence and/or post-emergence.

19. A method of controlling plant growth at a locus comprising applying to the locus herbicidally effective amounts of (A) the crystalline modification I of 2-(4-mesyl-2-nitrobenzoyl)cyclohexane-1,3-dione (mesotrione) and (B) the crystalline modification I of sodium salt of methyl 4-iodo-2-[[[[(4-methoxy-6-methyl-1,3,5-triazin-2-yl)amino]carbonyl]amino]sulfonyl]benzoate (iodosulfuron-methyl-sodium), wherein the crystalline modification I of iodosulfuron-methyl-sodium exhibits each of the following reflexes as 2θ values in an X-ray powder diffractogram:

11.588±0.2

14.569±0.2

18.045±0.2

19.442±0.2

20.633±0.2

23.226±0.2

26.145±0.2

27.199±0.2

27.877±0.2

29.090±0.2.

20. The method according to claim 19, wherein the plant growth is being controlled in a crop selected from the group consisting of cereals, sugarcane and vegetables.

21. The method according to claim 19, wherein (A) and (B) are applied to the locus at the same time.

22. The method according to claim 19, wherein (A) and (B) are applied to the locus consecutively.

23. The method according to claim 19, wherein the plant growth being controlled is selected from the group consisting of one or more of broadleaf weeds and grasses.

24. The method according to claim 23, wherein the plant growth being controlled is selected from the group consisting of one or more of *Chenopodium* spp., *Polygonum* spp., *Stellaria* spp., *Amaranthus* spp., *Amaranthus* spp., *Ipomoea* spp., *Veronica* spp., *Fallopia* spp., *Brassica* spp., *Galium* spp., *Xanthium* spp.

25. The method according to claim 19, wherein the weight ratio of (A) to (B) applied is in the range of from 150:1 to 1:50.

26. The method according to claim 25, wherein the weight ratio of (A) to (B) applied is in the range of from 50:1 to 1:10.

27. The method according to claim 26, wherein the weight ratio of (A) to (B) applied is 10:1.

28. The method according to claim 19, wherein (A) and (B) are applied at an application rate of 0.005 kilograms/hectare (kg/ha) to about 5.0 kg/ha of the total amount of active ingredient (A) and (B).

29. The method according to claim 28, wherein (A) and (B) are applied at an application rate of from 0.01 kg/ha to 3.0 kg/ha of the total amount of active ingredient (A) and (B).

30. The method according to claim 29, wherein (A) and (B) are applied at an application rate of from 1 to 1000 g/ha of (A) and from 0.1 to 250 g/ha of (B).

31. The method according to claim 30, wherein (A) and (B) are applied at an application rate of from 1 to 150 g/ha of (A) and 1 to 80 g/ha of (B).

32. The method according to claim 19, wherein (A) and (B) are applied pre-planting, pre-emergence and/or post-emergence.

* * * * *